US009410937B2

(12) United States Patent
Fougere

(10) Patent No.: US 9,410,937 B2
(45) Date of Patent: Aug. 9, 2016

(54) METHOD OF OPERATING A SMALL-SCALE WATER SEPAROMETER TO PRE-TREAT A FILTER PRIOR TO TESTING A FUEL SAMPLE

(71) Applicant: Alan James Fougere, Falmouth, MA (US)

(72) Inventor: Alan James Fougere, Falmouth, MA (US)

(73) Assignee: D-Z INC., N. Falmouth, MA (US)

( * ) Notice: Subject to any disclaimer, the term of this patent is extended or adjusted under 35 U.S.C. 154(b) by 128 days.

(21) Appl. No.: 14/499,473

(22) Filed: Sep. 29, 2014

(65) Prior Publication Data
US 2015/0093833 A1    Apr. 2, 2015

Related U.S. Application Data

(60) Provisional application No. 61/884,025, filed on Sep. 28, 2013, provisional application No. 61/884,017, filed on Sep. 28, 2013, provisional application No. 62/043,314, filed on Aug. 28, 2014.

(51) Int. Cl.
*G01N 33/18* (2006.01)
*G01N 33/28* (2006.01)
*C10L 1/00* (2006.01)
*G01N 33/22* (2006.01)

(52) U.S. Cl.
CPC ............ *G01N 33/2847* (2013.01); *C10L 1/003* (2013.01); *G01N 33/22* (2013.01)

(58) Field of Classification Search
CPC ................................ G01N 33/18; G01N 33/22
USPC ....................... 436/39–40, 166, 172, 177–178
See application file for complete search history.

(56) References Cited

U.S. PATENT DOCUMENTS 3,478,578 A * 11/1969 Dukek ............... G01N 33/2847
356/441
3,824,823 A *  7/1974 Pontello ................. B01D 35/00
73/38

(Continued)

OTHER PUBLICATIONS

ASTM D3240—15 2015, 5 pages.*

(Continued)

*Primary Examiner* — Arlen Soderquist
(74) *Attorney, Agent, or Firm* — Milton Oliver

(57) ABSTRACT

The safety and proper performance of jet aircraft engines requires that any contamination of jet fuel, for example by water or by improper contaminants, be filtered (removed) before delivery of the fuel, through hoses, to the fuel tanks of the aircraft. Coalescing devices and filters in the fuel delivery system are used to attain this result. A typical problem is that filter materials chemically react with surfactants, and this causes the filter subsequently to "disarm" or fail to perform its function of removing water, which can lead to delivery of fuel containing excessive water. A solution to this problem is to pre-test the fuel for such surfactants by feeding a small fuel sample that has been mixed with "challenge water" through a smaller 'representative' test filter and monitor the performance. Using a fluorescent dye in the "challenge water," the amount of water that passes the test filter is detected, compared with a baseline data and fuel quality determination is made. From the result of the small-scale test, the fuel condition can be inferred and, based thereon; action can be taken to treat the fuel, prior to further distribution, such that it will not disarm field filter-coalescers in a typical fuel distribution system. The use of a fluorescent dye enhances the ability to make this determination of very small representative fuel filters. The fuel evaluation process is fully automated, thereby avoiding human-factor variables and assuring repeatable results.

2 Claims, 2 Drawing Sheets

(56) References Cited

U.S. PATENT DOCUMENTS

| | | | | |
|---|---|---|---|---|
| 3,873,271 | A | * | 3/1975 | Young .............. G01N 33/2847 |
| | | | | 206/524.8 |
| 4,362,630 | A | * | 12/1982 | Young .................. B01D 15/00 |
| | | | | 206/524.8 |
| 4,513,606 | A | * | 4/1985 | Rhynard ............ B01D 17/0214 |
| | | | | 210/85 |
| 8,017,020 | B2 | | 9/2011 | Hoskin ........................ 210/739 |
| 8,354,069 | B2 | * | 1/2013 | Eastwood ............. B01D 11/04 |
| | | | | 205/687 |
| 8,356,618 | B1 | | 1/2013 | Werner ......................... 137/172 |
| 8,590,493 | B1 | | 11/2013 | Torgerud ........................ 123/25 |
| 8,720,499 | B2 | * | 5/2014 | Kastner ..................... B64F 1/28 |
| | | | | 141/192 |
| 2004/0020106 | A1 | * | 2/2004 | Tack ........................ C10L 1/143 |
| | | | | 44/393 |
| 2005/0223629 | A1 | * | 10/2005 | Sutkowski .............. C10L 1/143 |
| | | | | 44/397 |
| 2009/0023223 | A1 | * | 1/2009 | Eastwood ............. B01D 11/04 |
| | | | | 436/172 |
| 2009/0289013 | A1 | * | 11/2009 | Hoskin ................. C10G 33/06 |
| | | | | 210/739 |
| 2013/0270192 | A1 | * | 10/2013 | Chase ................. B01D 17/045 |
| | | | | 210/708 |
| 2015/0090012 | A1 | * | 4/2015 | Fougere ................. C10L 1/003 |
| | | | | 73/61.46 |

OTHER PUBLICATIONS

Trifilieff, O. et al, "Improve Hydrocarbon Condensate Dehydration Performance—Diagnostics and Solutions" Gas Processors Association (GPA) Europe Spring Conference May 25-27, 2011, Copenhagen, 16 pages.*

Fougere, A "Novel New Microseparometer Method" Gulf Coast Conference, Galviston, TX 2011, 10 pages, downloaded from http://www.gulfcoastconference.com/2011_Presentations/Novel_New_Micro_Separometer_Method.pdf.*

Velcon Filters LLC,"API 1581, $5^{th}$ Edition Specification Key Points," © 2009, pp. 1-2.

Emcee Electronics Inc, Venice FL, "Model 1140 Micro-Separometer," retrieved Nov. 2, 2014, pp. 1-4.

ASTM.org of PA, "ASTM D3948 Standard Test Method for Det. Water Separation . . . "retr. 2014, pp. 1-3.

ASTM.org of PA, ASTM D1655 Standard Specification Aviation Turbine Fuels, retr. 2014, pp. 1-4.

Wikipedia, "JP-8 = Jet Propellant 8" article, retrieved Sep. 28, 2014, pp. 1-5.

Microchip Technology, Chandler AZ, "dsPIC30F5011/5013 Controllers," © 2011, excerpt pp. 3-13.

Reach Technology, Fremont CA, "Standard Display Module 51-0105-02" flyer, retr. 2011, p. 1.

Lee Company, Westbrook CT, "LEE Fluid Control Products" webpage, retr. 2014, pp. 1-2.

KNF Flodos AG, Switzerland, "FMM20 Magnetic Diaphragm Metering Pump," retr. 2014, pp. 1-6.

Wikipedia, "Fluorescein," article retrieved Nov. 4, 2014, pp. 1-7.

Perkin-Elmer.com, Shelton CT, "An Introduction to Fluorescence Spectroscopy," © 2006 , pp. 1-16.

Cree Inc., Durham NC, "CREE C503 Series Color LEDs," retrieved Nov. 2014, pp. 1-6.

Hamamatsu Photonics, Japan, "Si Photodiodes with preamp," retrieved Nov. 2014, pp. 1-7.

* cited by examiner

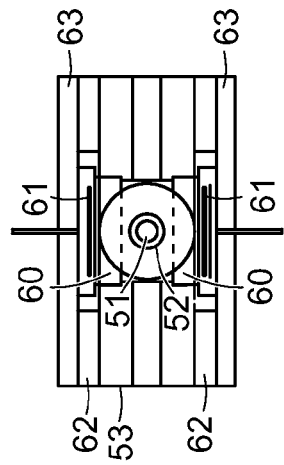
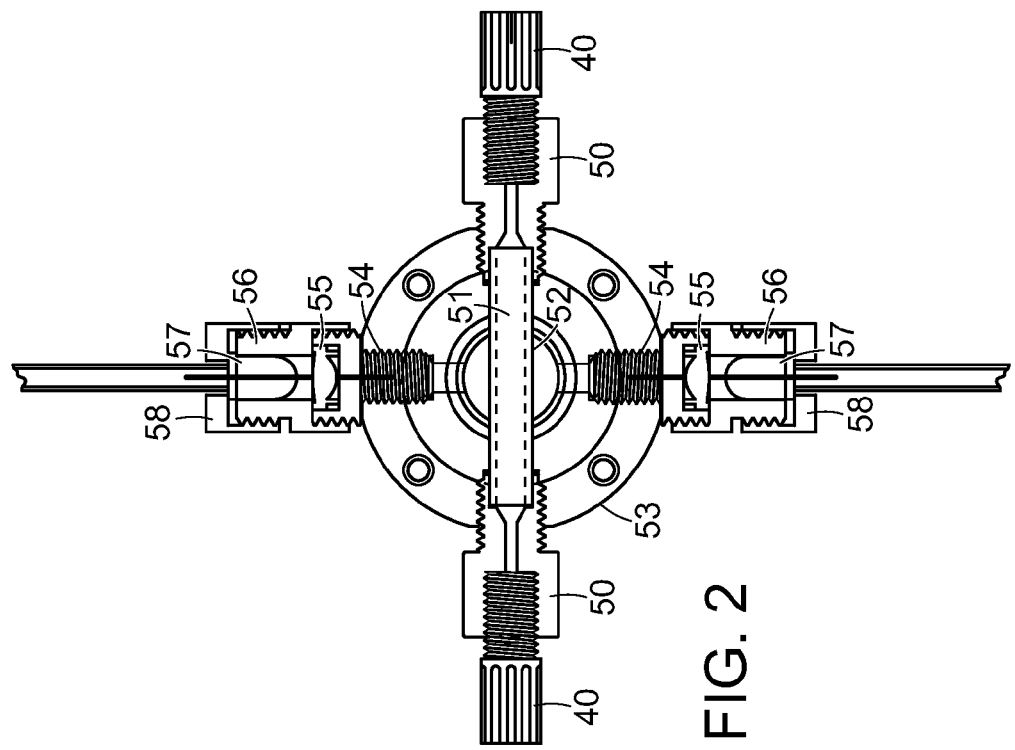

METHOD OF OPERATING A SMALL-SCALE WATER SEPAROMETER TO PRE-TREAT A FILTER PRIOR TO TESTING A FUEL SAMPLE

CROSS-REFERENCE

This application claims priority from my U.S. provisional application Ser. Nos. 61/884,025 and 61/884,017 filed Sep. 28, 2013 and 62/043,314 filed Aug. 28, 2014, the entire contents of which are hereby incorporated by reference.

FIELD OF THE INVENTION

The present invention relates generally to an instrument that makes improved measurements of surfactant levels in turbine aviation fuels, in order to predict to what extent, if any, these specific fuels will degrade the ability of modern fuel-water coalescer/filters to separate water from fuel. This improved instrument is known in the industry as a "small-scale separation tester." Aviation fuel providers need accurate assurance that water filter-separators will not be harmed by, or "disarmed" by, chemicals present in the fuel they are filtering.

BACKGROUND

Aviation fuel is vulnerable to contamination from a number of sources through the fuel distribution system. Contamination takes many forms, from trail-back in pipeline systems, to leaking roofs in holding tanks, or to treatment by wrong (non-approved) additives. Since the ultimate goal of the aviation fuel system is to deliver 100% "fit for purpose" fuel to the skin of the aircraft, it is essential that contamination problems, which arise along the fuel distribution path, be rapidly assessed.

One contamination issue that must be reduced to a minimum level is free water in fuel. Free water can result in microbiological growth in aircraft fuel tanks, poor engine performance or, at worst, a complete failure of the aircraft's ability to safely operate. Free water in an aircraft fuel system is removed by water separator coalescence filters or by still-tanking fuel until gravity causes the water (specific gravity about 1.0) to separate out of the aviation fuel (specific gravity about 0.8) and collect at the bottom of the tank or other container. Modern airport fueling systems often include coalescers which remove free water, prior to fuel reaching the skin of the aircraft. Modern filter coalescers use a variety of materials to accomplish the separation of free water. At the time of this writing, water filter-coalescers approved for use by the American Petroleum Institute (API) employ materials specified by the API 1581 standard ($5^{th}$ Edition). These materials are typically special fiber-type polymer materials. The performance of these filter materials can be adversely affected by chemicals in aviation turbine fuel (jet fuel), often referred to as "surfactants." Surfactants are surface-active chemicals which impair the ability of coalescer materials to aggressively remove free water. This chemical deterioration of filter performance is referred to, in the industry, as "disarming" the water filter. Hence, the ability to test fuels as to their chemical interaction behavior in modern API 1581 filter-coalescers is an essential element of safe operation of aircraft fueling operations worldwide. The goal of filtering is to supply fuel to the aircraft that meets all aircraft specifications. Aviation turbine fuel cleanliness specifications are set forth in two main standards. One widely recognized standard is overseen by the ASTM International (formerly American Society for Testing & Materials) specification D1655-14. A second standard is managed by the British Ministry of Defense: specification DefStan 91-91. There are also related standards for specialized fuels, for example: the United States Department of Defense MIL-DTL-83133 for JP-8 type fuel. I have invented a system and method, by which a small sample of a specific fuel is evaluated in a rapid and fully automatic laboratory instrument, to accurately access if that sample contains harming surfactants that may affect the water separation performance of large field-deployed filter coalescers. This system and method can be adapted for use with newer filter materials as the API 1581 $5^{th}$ edition specifications change to subsequent editions of the standard (see www.API.org). Note, although as described herein for surfactant testing in aviation turbine fuel, the instrument can also determine surfactant level effects on water separation characteristics of other distillate fuels, for example, of diesel fuel.

Water separation instruments ("Separometers") are commonly categorized as either "large scale"/"full-scale" (bulky and stationary) or "small-scale" (portable). Making a "small-scale" instrument as accurate as a "full-scale" instrument has been regarded as technically difficult. The method of the present invention relates to the preconditioning of the filter in a small-scale separometer. Modern fuel-filter "stands" operate for long periods of time, often without the presence of any free water. "Stand" is an industry term which refers to a set of filters that are used to treat fuel at a specific location, as the fuel moves through a delivery system. For example, in the United States, a Jet Fuel Filter Stand typically consists of three sequentially arranged filter vessels: first a clay treating vessel, then a coalescer vessel, and finally a particulate vessel. In fact, this is the normal operating condition, since modern fuel delivery systems are often equipped with free water removal filters or methods throughout the distribution system. In fact, the fuel delivery system is often described by industry insiders as "over-filtered." Surfactants are detergents, surface active chemicals, which will chemically behave differently in the presence of water. Surfactant occurrence in fuels can be the result of byproducts of the crude oil refining process, or they could be subtle side-effects of approved additives, or worse, from the addition of non-approved additives. Fuel additives are commonly used to modify the performance or physical characteristics of fuels. For example, Static Dissipative Additive (SDA), which is added to improve the electrical conductivity of fuel and to reduce the potential for electrostatic build-up of electrical charge in fuel, is also known in the industry to behave as a weak surfactant. When in the presence of free water, these surfactant chemicals are much more likely to react with the highly-polarized water molecules than with the fuel itself. Hence, water actually tends to reduce interaction between surfactants and the surface of the filter media. Hence, the "reactivity" (the ability to disarm a filter coalescer) of these surfactant chemicals changes, as the availability of free water in the subject fuel changes.

Traditional water separation determination instruments, which measure the ability of water to be coalesced, have not taken into account this water reactivity of surface-active ingredients. In fact, the current prevalent test (ASTM D3948), for determining potential surfactant levels in fuel, first mixes the fuel/surfactant with a high level of free "challenge" water, ~1000 ppm, to form an emulsion. This emulsion of water/fuel/surfactant is then presented to the test filter medium. However, in this test, since the test fuel/surfactant has already been mixed with the challenge water, in high concentration, the available surfactants may not react with the filter material to the same extent as they would without the presence of the filter challenge water. This mixing of water into the test fuel impairs the ability of the existing determination method, as described by ASTM D3948, to accurately predict whether or not a particular test fuel will disarm field water filter-coalescers.

SUMMARY OF THE INVENTION

My solution to this accuracy problem is to modify the testing procedure in the "small scale test" such that the water/surfactant fuel is first pre-conditioned (passed through) the test filter media in the absence of free water. Experiments have shown that this pre-conditioning in fact more than doubles the water separation instrument's response to the presence of an identical concentration of surfactants in a test fuel. Hence, a larger instrument response, as direct result of the pre-conditioning step, provides, to the instrument user, an ability to attain more accurate determinations of a given fuel's propensity to disarm a field water separator-coalescer. This preconditioning also more closely models the actual operation of a full-scale filter-stand. Typically, in the field filter stand, the coalescing materials are constantly reacting with surfactants in the fuel, in the absence of free water. As we have shown, this interaction significantly increases the "disarming" effect of the surfactants. The "pre-conditioning" in the small-scale separometer thus more closely mimics what is happening in the (larger) field filter stand. As it is the goal of the small-scale separometer instrument to accurately predict "field filter stand performance", this preconditioning step results in a significant improvement in the small-scale separometer's predictive result.

This pre-flushing though the filter materials, prior to the application of the "water challenge," is novel and inventive when applied to the performance of small-scale water separation instruments.

Conventional separation devices, such as the instruments listed in ASTM (American Society for Testing & Materials) method D3948, have shown their inability to reliably detect the presence of some mild to strong surfactants, and, while at the same time, those devices often indicate false-positive readings, in response to mild or weak surfactants.

This performance in existing small-scale testing equipment is contrary to what the industry experiences with its full-size filter stands; as a result, the industry needs more reliable small-scale separometer predictive results. Current unreliable small-scale separometer results often cause fuel industry participants to take unneeded fuel remediation steps, such as clay-treating large volumes of fuel. Generally, unnecessary "remediation" steps take extra time, and delay delivery of fuel to the aircraft which need the fuel to keep flights on schedule. Such false-positive surfactant readings by the current version of small-scale separation instruments have resulted in fuel suppliers having to provide remediation of fuel, by filtering through clay. This clay filtering was not, in fact, necessary because the false-positive result was simply due to a misleading reading from the instrument, and not really due to a "failing" fuel having unacceptable contamination. A worse possible outcome is delivery of fuel containing a significant quantity of free water when the prior art test gives a false-negative indication, (low surfactant contamination), but in fact surfactants are present that do disarm the filter stand, and thereby allow water to pass into the fuel delivered to an aircraft. This failure of the prior art testing technology, to properly indicate surfactant levels, could result in a catastrophic outcome for the operator of turbine-driven aircraft, for example if the water causes more than one engine to fail.

I have demonstrated, in the laboratory, that the pre-flush is an essential requirement in a small-scale separometer to obtain accurate filter stand predictive performance. The duration and amount of fuel needed to carry out the method can be adjusted, due to a specific filter material performance, but the preconditioning improves the ability to obtain accurate small-scale separometer results.

The present invention allows a fuel user/supplier to rapidly and confidently evaluate their ability to test a fuel for its ability to have its water coalesced out or, in other words, the potential that a specific fuel will tend to "disarm" those water coalescers which are in common use.

Chemicals that potentially interfere with fuel/water separation can occur in concentrations of less than 1 PPM; hence, the direct measures of these chemicals by other methods or techniques can be time-consuming and technologically complicated. At small concentrations, it can be difficult to detect the presence of the chemical(s). Since the specific interest of the fuel supplier is to determine the ability of a subject fuel to be water-separated and filtered, it is always the best practice to test this ability directly. In the current invention, a filter of the standard industry-approved material is subjected to a "water challenge." The filter is presented with raw fuel under test, such that any chemical or surfactant in the fuel is deposited onto the filter, or reacts with the filter, in the same manner as could be expected in a large-scale filter-stand, without the presence of free water. The subject fuel is then blended with specially dye-treated water and then emulsified by the use of a sonic acoustic-cavitation mixing wand, in order to optimize the size distribution of water droplets.

A novel aspect of this automated system is the use of fluorescent dye, to allow very high-resolution measurement of the quantity, if any, of water in the fuel sample that passes the filter during the "water challenge" portion of the test. The use of a fluorescent dye facilitates detection of any water passed by the filter, in levels as low as <1 Part Per Billion, (PPB). The use of fluorescent dye for water-tracing fluids is not new or novel, per se; however, the use of such dye material, to enhance the ability to determine whether or not small-scale fuel filters can perform in the presence or absence of interfering chemicals, is novel, and is a critical aspect of the method and instrument of this invention.

The use of a sonic acoustic cavitation wand, for mixing of the "challenge water" into the test fuel, is another novel aspect of this invention, since filter-coalescer performance is highly dependent on water droplet size. Prior art methods and instruments which use simple hand blenders for mixing purposes, may, or may not, develop consistent droplet size. The existing hand blenders tend to yield variable emulsions, based on a specific operator's technique, resulting in additional variance in the results obtained. The use of a fixed, power-regulated, acoustic sonic mixer results in emulsifications which are highly consistent, and which have eliminated all operator influence on the characteristics of the test water/fuel emulsion.

BRIEF FIGURE DESCRIPTION

The following figures, which are not intended to limit the invention, illustrate a preferred embodiment:

FIG. 2 is an enlarged side view of the fluorescence detector which is part of the system of FIG. 1; and FIG. 3 is a longitudinal cross-section through the same fluorescence detector shown in FIG. 2.

DETAILED DESCRIPTION

Figure 1:
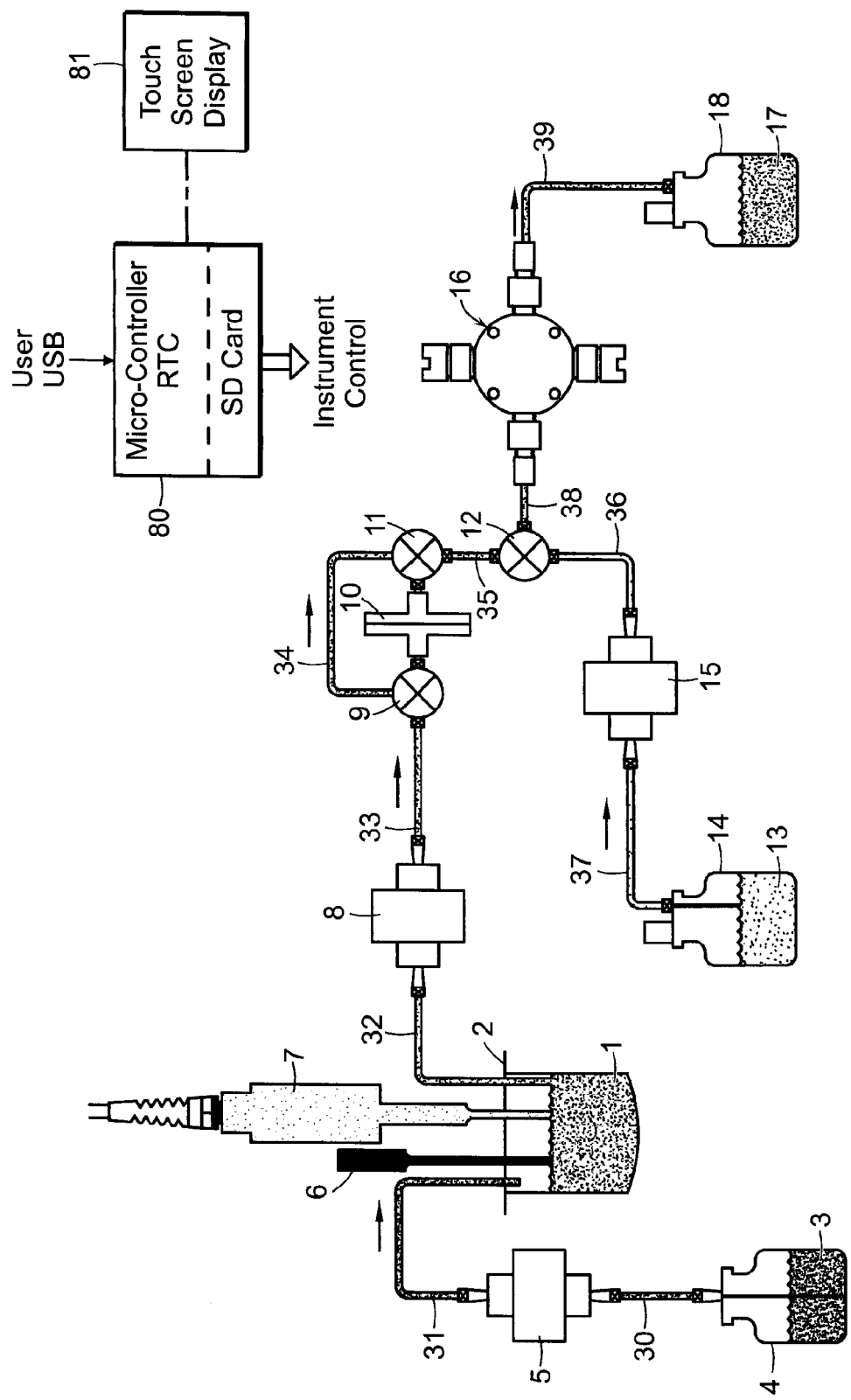
FIG. 1 is a block diagram of an implementation of the fuel evaluation system, adapted for performing an automated evaluation.

FIG. 1 schematically illustrates a testing system, adapted for performing the method specified in ASTM D3948, in which three different fluids 1, 3, 13 are fed in, and a fluid waste 17 comes out at a downstream end, shown at right. For ease of comprehension, individual electrical data collection lines to, and electrical control lines from, a microcontroller 80 have been omitted from the figure; how to make such connections is apparent to a person having ordinary skill in the field of instrumentation design. The three input fluids are a fuel sample 1, held in a sample container 2, dye-treated water 3, held in a reservoir 4, and a solvent 13, held in a reservoir 14. A temperature probe 6 and a sonic mixing wand 7 extend downward into the fuel sample 1, held in sample container 2. Temperature probe 6 is used (1) to confirm, before testing, that the fuel sample is within the 20-30 degree C. specified in the ASTM standard; (2) to measure how much sonic mixing has warmed the fuel sample (typically 1 to 2 degrees C.); and (3) to measure temperature at the end of a data run, for archival purposes. A water pump 5 can withdraw dye-treated water 3 via a tube 30 from reservoir 4, and supply it via a tube 31 to sample holder container 2. Preferably, the dye is one which fluoresces in response to excitation by light, as described in more detail, below. Mixing wand 7 can emulsify the resulting mixture of fuel and dye-treated water, which is then withdrawn via a tube 32 by a main pump 8, which then sends the emulsion along a tube 33 to a first valve 9. Depending upon its setting, valve 9 either feeds the emulsion, via a by-pass tube 34, to a second valve 11 or applies it to the input side of a filter-coalescer 10, whose output side also connects to second valve 11. An output side of second valve 11 connects via a tube 35 to a third (three-port) valve 12.

According to a novel feature of the system and method of the present invention, a solvent pump 15 can withdraw solvent 13 via tube 37 from reservoir 14, and supply solvent 13, via tube 36 to valve 12, and thence via a tube 38 to an input side of optical detector 16, when it is desired to flush optical detector 16. An output side of optical detector 15 connects via a tube 39 to a container 18 for waste fluid 17.

The testing or evaluation system is controlled by a microprocessor 80 (suitable model: dsPIC30F5011 available from Microchip Technology Inc. of Chandler, Ariz., USA). As the manufacturer's datasheet describes, this device has a number of internal timers which are adapted to precisely time the durations of events, according to the present invention, controlled by the device, for example logic levels from microprocessor via 80 lead to various pumps, valves, and mixer on/off control. A Universal Asynchronus Receiver Transmitter, (UART), contained within microprocessor 80 is connected via a RS-485 Bus to sensors shown in FIG. 1, including the optical detector 16, the temperature sensor 6, and optional auxiliary sensors (not shown) such as a sensor for electrical conductivity of the fuel sample. A 5-second clock is established in the microprocessor or microcontroller 80, which runs a virtual "state machine" used to control the process for determination of a "water separation" or "WSI" value which is characteristic of the specific fuel being tested. Each state runs a process; for example, "state 2" runs an operation which pre-flushes optical detector 16. The number of 5-second intervals that the "state 2" runs is a variable, which is preferably saved in Electrically Erasable Programmable Read-Only Memory (EEPROM). Therefore, the duration of each of the process "states" can be adjusted, for example using a touch screen display 81 as the user interface. The microcontroller 80 also using Digital to Analog Convertor's, (ADC') can control pump rate control signals and sonic mixer amplitude signals.

All data are collected from the detector 16 via the RS-485 data bus. The detector has its own microprocessor (suitable model: dsPIC30F3011 available from Microchip Technology Inc. of Chandler, Ariz., USA). This distributed microprocessor control allows each device to focus on its specific function, eliminating latency errors or device overload. In addition, the microcontroller 80 interfaces with an SD memory card, which is used to store each run in IBM-DOS compatible data file format. Microcontroller 80 is also equipped with a Real-Time Clock (RTC), to time and date-state each data run. The user starts the process using a touch-screen display panel 81 (e.g. model 52-0103-03 or 52-0104-23 available from Reach Technology Inc. of Fremont Calif. & Lake Oswego, Oreg., USA), which is connected to the main microcontroller via an RS-232 full-duplex data link. The user can monitor each data run, via the touch screen display 81. The display also give the user options to run diagnostics, calibrations such as water injection volume, sample pump flow rate, as required for proper instrument operations. The touch screen also warns the user of water/dye source level, solvent level and time-to-empty waste container levels. The user can make adjustments in parameters via the touch screen, and all changes are stored in an EEPROM data portion of the microcontroller 80.

Discussed in the previous sections are the detailed components used in evaluating the ability of the fuel to be successfully filtered. The following section discusses the method steps which the instrument performs, which steps are novel and are critical to obtaining precise, repeatable results. Each step of the process is controlled by the state machine also described in previous sections.

1) The user places a ~220 mL fuel sample 1 in a beaker 2 on the Water Separation Instrument (WSI), hereinafter the "system".

2) The user inserts a disposable filter cartridge 10 into the system, between valves 9 and 11. The filter's cross-sectional size is appropriately scaled to the volume of the fuel sample 1. In the current implementation, this cross-section is preferably ¼ in$^2$ (160 mm$^2$). Several different sizes are available on the market, and are used for practicing the method of ASTM standard D3948.

3) The user presses "start" and the system, based on a program stored in controller 80, runs the complete sequence of process steps as fully described below, automatically. In that manner, each step of the water separation value determination is precisely timed, and is completely repeatable, which represents a significant improvement over prior art manually operated methods and devices, used for similar purposes.

4) DETECTOR FLUSHING. The process commences by a cleaning of detector 16 by aggressive flushing, using solvent fed by a pump 15, from a reservoir 14 via valve 12. The solvent used is Isopropyl Alcohol (IPA) 13, contained in reservoir 14. The IPA is pumped through detector 16 by the constant-rate pump 15 (e.g. KNF 1.5NF pump available from KNF Flodos AG of Sursee, CH-6210) through a directional valve 12. The solvent passes through detector 16, and flows directly to a waste container 18. The IPA reduces the surface tension of any water that may be residing in the detector 16 and flushes it out, thereby ensuring that the system starts the fuel-evaluation process at a "zero" value for detected water.

5) INITIALIZATION. After the flushing or cleaning of the detector 16, the measurement process begins. The start of the process is to fill all tubing connections, including tube 32, using sample fuel pump 8 (ex KNF 1.5NF pump), tube 33, valve 9 (e.g. LFRA type from the Lee Company of Westbrook Conn., USA), tube 34, valve 11, tube 35, detector 16, and tube 39 are all filled with the current fuel sample 1. This process step takes ~10 seconds of pumping by main pump 8, which typically runs at a rate of ~25-30 ml/min.

6) FILTER PRE-FLUSHING. After the sample fuel has been filled through the device, a critical and novel step of the process is the pre-flush of filter 10. This novel step is important for a number of reasons as described in previous sections. One function performed also during the pre-flush is that a "baseline" reading for the fuel is made by optical detector 16. Fuels vary considerably, due to type of refining, base crude stock, additives, and, contaminants picked up along the distribution system. Some of these elements change the color, and or have their own fluorescence, which can cause the detector's response to vary from what one would expect. The detector 16, detailed in FIGS. 2 & 3, is a custom-designed optical cell which has a light source which applies light of an appropriate first wavelength to "excite" the fluorescent dye dissolved in the free water added to the fuel, two photo detectors 61, oriented orthogonally to the excitation light 57, which are used with optical filters 60 that remove all wavelengths except the (second) wavelength of light that is emitted as a result of the dye's fluorescence.

During the pre-flush of filter 10, a baseline detector value which is specific to the fuel under test is established by the detector 16. The pre-flush is performed by the fuel pump 8, pumping fuel at the same rate as the initial fill: 25-30 ml/min. Flow directional valves 9 and 10 are set so that the flow path is through the filter 10, rather than along bypass tube 34. Typically, flow is run through the filter 10 for 1 minute, or 25-30 ml of fuel. At the end of this period, pump 8 is stopped and a baseline value or reading is established by the detector 16. This baseline value is then subtracted from all subsequent readings, used to obtain the final "WSI" measurement value. The pre-flush is nominally run for 1 minute; hence ~25-30 ml of the sample is used for this process. Nominal baseline values are in a range between 100 and 200.

The second important aspect of the pre-flush is that raw fuel is passed through the filter 10, allowing any chemicals/surfactants in the fuel that can interfere with process of coalescence by the filter to react with the filter material in the absence of free water. At the conclusion of the pre-flush, the main sample pump 8 is stopped, the flow directional valves 9 and 11 are repositioned to bypass the filter 10, and the water injection followed by mixing cycle begins.

6) WATER INJECTION. The next process step is to mix the test free water 3 into the fuel to "test" the ability of filter 10 to separate water from the fuel. This is achieved using pump 5 to supply the water from reservoir 4, and sonic mixing wand 7 to mix it within tank 2 with fuel 1. The mixing cycle commences by injecting, into the fuel sample by pump 5 (e.g. model FMM20 solenoid magnetic drive type diaphragm metering pump, available from KNF Flodos of Sursee, Switzerland CH-6210), a predetermined volume of water 3 with a dye concentration. Pump 5 is a precision injection-solenoid-type pump; each time the solenoid in the pump is activated, it moves a precise amount of fluid. In the case of this device, the pump is calibrated by the manufacturer to inject 5 uL for each stroke of the solenoid. To gain sufficient sensitivity, the water dye 3 contained in vessel 4 has a concentration ratio which can be adjusted. In the case of this device with the current filter cross-sectional size, fuel sample size, and water to fuel dilution, I inject 60 uL of the water/dye mixture, requiring 12 cycles of pump 5. The water/dye to fuel ratio is selected such that a very stable emulsion is obtained in tank 2. The prior art devices use a very high concentration of water in the fuel, approximately 1000 parts per million (ppm). I have found that this high value causes inaccuracies, since the fuel simply cannot support in a stable mixed emulsion these high concentrations. As a result, I have chosen, based upon experimental results, to use a 300 ppm water to fuel ratio, i.e. 60 uL/200 mL (where 200 mL represents the sample minus the pre-flush). A novel aspect of the device is that a fluorescing dye (typically fluorescein) is used; this dye is fully hydrophilic; as such, the concentration of dye in the challenge water can be varied to "optimize" the signal level in the evaluation system. For example, as it was desirable to use an emulsion stable 300 PPM water to fuel concentration, in order to retain sensitivity in the detector, the dye concentration in the test water is increased to a concentration level where the resulting signal level in detector 16 allows for very high discrimination of water in the sample fuel. Hence a novel aspect of the present invention is the use of a hydrophilic fluorescent dye which can be detected down to levels of a fraction of one part per billion; there is a wide choice of alternative water-soluble fluorescent dyes, which could be used by one having ordinary skill in the art, with a corresponding choice of optical excitation wavelengths and optical detection wavelengths.

The preferred dye, Fluorescein, along with other suitable fluorescent dyes and wavelengths are shown in the table below:

| DYE MATERIAL | EXCITATION PEAK λ (nm) | EMISSION PEAK λ (nm) |
|---|---|---|
| Acridine Orange | 502.1 | 526 |
| Carboxynapthofluorescein | 598.9 | 674 |
| Cascade Blue BSA | 401 | 419 |
| Fluorescein | 489.9 | 513.2 |
| Lucifer Yellow CH | 427.9 | 544 |
| Magnesium Green (Mg2+) | 507 | 531 |
| Nile Blue | 630.5 | 660 |
| Nile Red | 553 | 636.9 |
| Oregon Green 488 | 504 | 536 |
| Pro-Q Emerald 300 reagent | 300 | 530.1 |
| Rhodamine 110 | 497 | 519.9 |
| Sodium Green (Na+) | 507.2 | 532 |
| Texas Red dextran | 592 | 613.9 |

Which dye is preferred will largely depend upon the availability and cost of wavelength-matched emitters (e.g. Light Emitting Diode's, LED's), matched fluorescence optical filters, and photo detectors.

7) MIXING TO FORM EMULSION. Normally, a sonic wand mixer 7 is turned on during the water injection performed above, to help prevent large water drops from adhering to the sample cup or other structures in the container, pick up tube, or, thermometer 6. The sonic mixer is run for predetermined on/off intervals, to fully emulsify the water/fuel mixture. Typically the mixer cycles are 10 seconds ON, then OFF, and, typically 10 such cycles, which results in a temperature rise of 1 to 2 degrees C. in the fuel/water sample. An example of a commercially available sonic mixer is the Sonics & Materials CV245 Convertor, with 630-0509 tip, driven by acoustic constant power amplifier (KITVC544), all from Sonics & Materials Inc. of Newtown, Conn. The use of an acoustic sonic cavitation mixer is a novel aspect of this invention, compared to the prior art. Acoustic sonic mixing is preferred over mechanical mixing because the sonic mixer has the ability to repeatedly apply a precise amount of mixing energy to the fuel/water sample. This results in very uniform test-to-test water/fuel emulsions where most importantly the majority size of the water droplets in the emulsion distribution is known to be ~20 micron, and, as important, known to be stable emulsion for much longer than the duration of the test. The sonic mixing, through its process of cavitation, breaks the water droplets down in a very uniform manner which cannot be achieved by mechanical means. Sonic mixers are typically used in medical applications, since the high energy density at the mixer's tip is capable of breaking down cell membranes. In this device, the goal is to have "consistent" water droplet size because droplet size has a dramatic effect on the process of water separation in API-approved filter media. Droplet size effects are well known in the industry, and the industry has developed a very specific test which specifies droplet size for the "qualification" of fuel filter elements. In addition, the novel use of ON/OFF cycles during the mixing process allows the large droplets that have not yet been broken down by the high energy at the mixer tip to drop back down to the bottom center of sample holder 2, where they are directly below the tip of the mixer and are subjected to the high energy cavitation. The mixer 7 chosen delivers 20-50 W of acoustic energy at 40 KHz; a suitable mixer driver is the Sonics KITVC544 model.

7) REFERENCE TIME. The next sequence is the establishment of the reference value. The main sample pump 8 pump is started, and pumps the water/fuel emulsion through the filter bypass loop 34 as selected by valves 9 and 11. So the un-filtered water/fuel emulsion is passed directly through the detector 16. This is required because it is necessary to establish a base intensity value of fluorescence in the now-fully-emulsified water/fuel mixture. The intensity of the reference can vary, due to a number of factors: the exact volume of sample placed on the unit by the user, small deviations in the water injection pump, and/or different fuels attenuating light differently or having different base colors. The exact amount of light attenuation is fuel-specific due to its chemistry (resulting from variation in the way fuels are refined, example MEROX, or, Hydrotreated refining processes). A reference level is then established, based on the output of the detector; as mentioned above, the baseline value is removed from this value. Nominal values for the reference level are 800-1200 as measured by the detector 16. The reference establishment time is 1 minute; hence another ~30 mL of test sample is used. The sample pump 8 is then stopped.

8) FLUSHING OF DETECTOR. To clear the high value reference full water/fuel emulsions from the detector, the detector is again flushed with the solvent using pump 15. Solvent 13 is directed into the detector 16 by fluid steering valve 12. The controller 80 verifies that this has been completed, by monitoring of the values from the detector 16. Typically a flush requires 10 mL of IPA, pumped at a rate of ~30 mL/min.

9) FILTER TIME. The filter selection valves 9 and 11 are then set, such that the fuel/water emulsion sample 1 is now passed through the test filter 10. The sample pump 8 is restarted, and data from the detector are now logged in the system processor. If the fuel has low or zero surfactant levels, it is typical that, for the entire filtering period, no response from the detector is seen, i.e. 100% of the water/dye is removed from the fuel by the filter 10. Conversely, if surfactants are present, the performance of filter 10 will start to deteriorate, and water will start to pass through the filter. Water passing is detected in the detector by the fluorescence process previously described. The filter time periods last for ~250 second (125 mL of fuel is passed through the detector) and the data from the detector, minus the base line valve, are summed throughout this period. Sum values are typically in the range of 0-100,000.

10) COMPUTATION. At the completion of the filter time period, the detector is again cleaned with solvent, making it ready for the next sample. The WSI value is computed by dividing the reference value into a fixed nominal scaling value, as example 1000. The resultant scalar is then multiplied by the total detector counts as summed during the filter time. The result is subsequently scaled into user-familiar values and presented to the user on the instrument's front display. For example, 100 indicates a good quality "filterable" fuel, while 50 indicates a high-surfactant fuel which presents more filtering difficulties. This range for output values is chosen to match the "industry-standard" range of values historically used to represent the water-separation characteristics of a fuel sample by small-scale separator. In this context, the "fuel quality" number is a number in the range between 50 and 100.

DETAILED DESCRIPTION OF THE DETECTOR

As briefly described above, the detector is of a novel design. The requirements of the detector are that it has the sensitivity to measure water which has been treated with a fluorescent dye at a level of sensitivity appropriate for the device, to enable accurate and repeatable filter performance determinations. As mentioned above, there is a "limit" to the concentration of water which can be added to fuels, and still have a stable emulsion generated. Even when using a sonic mixer, experiments have shown that a maximum desired concentration of water in the fuel is <500 ppm.

The optimum concentration of fluorescent dye in water also has a maximum. This is related to the fact that the dye, when dissolved in the fluid, in this case water, must have both (1) a clear path from the light source(s) whose light radiation (at a first wavelength) "excites" the electrons in the dissolved dye molecules into higher orbits, and (2) a clear path for the light emitted (at a second wavelength) by the fluorescent dye molecules, when their electrons drop back into lower orbits, to reach the photo detector(s). If we consider the dye as analogous to tiny light bulbs floating in a stream, then one can imagine that, at some increased concentration, number of light bulbs, there is no incremental increase light output, because the added light bulbs either shadow the source energy, or shadow the fluorescent light emitted by other proximal light bulbs, i.e. by the other dye molecules. Experiments have shown that, for Fluorescein dye in water, the maximum reasonable concentration for optimum signal is ~1000 ppm. In terms of the device's overall measurement, one is looking to measure the <500 ppm water as it exits the filter. In order to make "reasonable" estimates of filter performance, one needs to be able then to detect less than 0.5 ppm of water in fuel. Taking the 0.5 PPM and the 1000 PPM concentration, the detector must have a 0.5 ppb "least detectable" sensitivity.

Another aspect is that the detector must have a measuring fluid volume and flushing length that is suitable to the needs of the device. Clearly a large volume with long optic path is optimum from an instrumentation standpoint, but is not well-suited to the various process steps used in the device. These steps require the sample to be fully flushed from time to time from the detector, all while maintaining a suitably small fuel-sample size. Clearly a device that required liters of fuel would not be practical from a user's perspective. A typical fuel sample retention container used in the industry is 1 liter, so the fuel sample size must be limited to a reasonable fraction of that total sample. In my opinion, a 250 ml sample (¼ of the volume of a typical fuel sample container) is reasonable. Hence, all of the aforementioned factors constrain the physical size of the optical detection elements of the detector.

Detailed in FIG. 2 is a horizontal cross-section of the novel fluorescent detector. Detailed in FIG. 3 is a vertical cross-section cut across the detection tube 52 of the novel detector. The fluid path for the detector starts with ¼-28 FB port fittings 50 (symmetrical). Each fitting is customized to fit a standard ¼-28 FB compression tube fitting 40, and to seal the detector fluid tube 52. The sample passes through the detector tube 52, where it is illuminated by light at the excitation wavelength of the Fluorescein dye, typically wavelength 495 nanometers (nm). This dye has an emission peak at 521 nm. To illuminate the dye, two Light Emitting Diodes (LEDs) 57 (e.g. CREE Inc. part # C503B-BAN-CY0C0461) are mounted in holders 56, and retained by a cover 58, opposing each other from opposite sides of the sample tube 52. The sample tube cannot be made from glass, due to the polarized nature of a glass surface. It is the polarized surface nature of glass that causes a meniscus in a test tube. The wall of a glass tube would, in effect, attract water out of the fuel emulsion and cause the water to stick to the tube wall, rather than pass through as part of an unchanged emulsion. Hence the tube is preferably fabricated from a material with a low surface energy, such as polycarbonate. A suitable diameter of the tube, to yield reasonable flushing and provide adequate dye concentration is ~0.25" (6.3 mm) O.D., with 0.2" (5.0 mm) I.D., while a suitable length is ~1.0" (25.4 mm). The excitation light from the diodes is collimated by a pair of aspheric lenses 55 (e.g. Edmund Scientific model #45-356), which are precisely positioned by holder 54, which also serves as a mount to the main body of the detector 53. The lenses collimate the light, to assist in preventing light from reflecting off the radius of the detector tube 52. The illuminating light (at a first wavelength) in the presence of the dye results in the dye emitting light (at a second wavelength) radially in all directions.

In order to gain as great a sensitivity to the radiated light as possible, two large planar photo detectors 61 (e.g. HAMAMATSU 58746-01) are oriented orthogonally to the excitation light path. These are also held in precise position by mounting on printed circuit boards 62, which are positioned by the main body of the detector 53. To assist in the rejection of light from the source LEDs 57, light filtering is provided by two glass optical filters 60 (e.g. Edmund Optics Stk #67-044) which are placed in the path of the fluorescent light to the detectors 61. Finally, in order to protect the detector from changes in ambient light, a cover 63, constructed from opaque material, covers detector 16. In laboratory testing, detector 16 has shown its ability to resolve fluorescein dye in concentrations of <0.5 PPB, in fluid flowing at 30 ml/min through the sample tube 52. Using precision dilutions, the response of detector 16 has been found to be stable, and linear to better than ½% of typical reading values. The detector 16 is provided with a microcontroller 80 as detailed in previous sections. The local microprocessor sets optical drive levels for exciting LEDs 57, and digitizes data from the optical detector chips 61. The microprocessor sums data from the two detector chips 61 and scales the results into a single result which is transmitted via the RS-485 bus to the main instrument controller.

The foregoing description represents a preferred embodiment, based upon components commercially available in 2014. However, to persons having ordinary skill in the instrumentation field, it will be apparent that numerous variations and modifications are possible, within the scope of the inventive concept, for example when better-performing or more energy-efficient components become available. Therefore, the invention is not limited to the embodiment as shown and described, but rather is defined by the following claims.

What is claimed is:

1. A method of evaluating to what degree a specific fuel sample will impair performance of a filter with a system for evaluation of a distillate fuel, said system having an input conduit (32) for a sample (1) of fuel;
   an input conduit (30) for a predetermined volume of water;
   means (7) for mixing said water into said fuel sample;
   a filter (10) adapted to separate water from said fuel sample; and
   a detector (16), downstream of said filter (10), for measuring any concentration of water remaining in said sample after passage through said filter (10);
   the method comprising the steps of:
   A) performing a pre-flush of fuel through the filter, prior to mixing the fuel with water, to ensure that any surfactants in the fuel are allowed to react with the filter (10) without any interfering effects of water, and to measure a baseline optical property value;
   B) mixing (7) using a controlled power ultrasonic cavitation mixer a sample (1) of fuel with a known amount of water (3) containing a fluorescent dye, thereby creating a water/fuel emulsion;
   C) feeding said water/fuel emulsion along a by-pass path (34) around the filter (10) to a fluorescence detector (16), in order to ascertain a reference level of fluorescence, and subtracting said previously obtained baseline optical property value from said reference level to derive a final detector output value;
   D) feeding said water/fuel emulsion through said filter (10) for a predetermined period of time, while monitoring a flow (35) emerging from said filter to ascertain whether, and at what rate, water is detected; and
   E) computing a WSI value by summing output values from the detector, each less the baseline value, from the filtered time, and, scaling that result by the reference value less the same baseline data, then scaling a resulting value into an industry-standard value range.

2. The method of claim 1, wherein the industry-standard value range is between 40 and 100.

\* \* \* \* \*